United States Patent
Pillar et al.

(10) Patent No.: US 8,541,194 B2
(45) Date of Patent: Sep. 24, 2013

(54) DETECTING MICRO-ORGANISMS IN AN ELECTROCOATING PROCESS

(75) Inventors: Lonnie L. Pillar, Forest Lake, MN (US); Michael J. Bourdeau, Prior Lake, MA (US); Michael A. Contos, Bettendorf, IA (US); Robert A. Sailer, Andover, MN (US)

(73) Assignee: Valspar Sourcing, Inc., Minneapolis, MN (US)

( * ) Notice: Subject to any disclaimer, the term of this patent is extended or adjusted under 35 U.S.C. 154(b) by 684 days.

(21) Appl. No.: 10/792,937

(22) Filed: Mar. 4, 2004

(65) Prior Publication Data

US 2004/0231988 A1 Nov. 25, 2004

Related U.S. Application Data

(60) Provisional application No. 60/452,132, filed on Mar. 4, 2003.

(51) Int. Cl.
*C12Q 1/06* (2006.01)
*C25D 11/00* (2006.01)
*C25D 15/00* (2006.01)

(52) U.S. Cl.
USPC .............................. 435/29; 204/471; 204/478

(58) Field of Classification Search
USPC ................................. 435/8, 29; 204/471, 478
See application file for complete search history.

(56) References Cited

U.S. PATENT DOCUMENTS

| | | | |
|---|---|---|---|
| 4,744,950 A | 5/1988 | Hollander | |
| 4,995,987 A | 2/1991 | Whitekettle et al. | |
| 5,234,958 A | 8/1993 | Donofrio et al. | |
| 5,278,188 A | 1/1994 | Whitekettle et al. | |
| 5,352,706 A | 10/1994 | Donofrio et al. | |
| 5,416,109 A | 5/1995 | Donofrio et al. | |
| 5,416,122 A | 5/1995 | Donofrio et al. | |
| 5,430,078 A | 7/1995 | Hoppe-Hoeffler et al. | |
| 5,430,479 A | 7/1995 | Takahama et al. | |
| 5,611,939 A | 3/1997 | Hernandez-Mena et al. | |
| 5,624,810 A * | 4/1997 | Miller et al. | 435/8 |
| 5,695,652 A | 12/1997 | Hernandez-Mena et al. | |
| 5,736,056 A | 4/1998 | Wright et al. | |
| 5,763,482 A | 6/1998 | Paterson et al. | |
| 5,891,702 A * | 4/1999 | Sakakibara et al. | 435/227 |
| 5,942,219 A | 8/1999 | Hendriks | |
| 5,997,812 A | 12/1999 | Burnham et al. | |
| 6,017,431 A | 1/2000 | Augustini et al. | |
| 6,066,479 A | 5/2000 | Wright | |
| 6,241,898 B1 | 6/2001 | Wright et al. | |
| 6,290,830 B1 | 9/2001 | Kaylo et al. | |
| 6,350,358 B1 | 2/2002 | Ehmann et al. | |
| 6,757,521 B1 | 6/2004 | Ying | |
| 6,872,291 B2 * | 3/2005 | Boyd et al. | 204/472 |
| 6,977,012 B2 | 12/2005 | Nobutoh et al. | |
| 6,977,013 B2 | 12/2005 | Schroeder et al. | |

| | | |
|---|---|---|
| 2001/0008649 A1 | 7/2001 | Layrolle et al. |
| 2003/0000837 A1 | 1/2003 | Kaylo et al. |
| 2003/0204560 A1 | 10/2003 | Chen et al. |

FOREIGN PATENT DOCUMENTS

| | | |
|---|---|---|
| CA | 2267678 | 4/1998 |
| CA | 2384195 | 4/2001 |
| CA | 2452014 | 1/2003 |
| DE | 19955372 | 5/2001 |
| WO | WO 99/03933 | 1/1999 |
| WO | WO 00/59834 | 10/2000 |
| WO | WO 01/62084 | 8/2001 |
| WO | WO 01/62091 | 8/2001 |
| WO | WO 03/004733 | 1/2003 |

OTHER PUBLICATIONS

Winkowski, K et al, "Controlling Microbial Contamination," Jul. 2002, Paint & Coatings Industry, vol. 18, Issue 7, p. 60-66.*
Paint and Coatings Industry, "Paint and the Constant Threat of Microbial Attack: Why a Constant Vigil is Needed," Jul. 2000, p. 64-74.*
Chu et al, "Using ATP Bioluminescence Technique for Monitoring. Microbial Activity in Sludge," (Biotechnology and Bioengineering), Nov. 20, 2001, vol. 75, No. 4., pp. 469-474.*
PCT Written Opinion for PCT/US02/006684, mailed Feb. 11, 2005.
Walker, "New microbiological monitoring nethodsfor water systems," *Spec. Chem.*, 1993, 13(3):110-111.
Canadian Official Action dated Oct. 19, 2007, for related Canadian patent application No. 2,517,550, filed Mar. 4, 2004, (6 pages).
First Examiner's Report by Canadian Patent Office dated May 14, 2008, for related Canadiam patent application No. 2,517,550, filed Mar. 4, 2004, (4 pages).
Mexican Official Action for Mexican Patent Application No, PA/a/2005/009254, received on Jan. 25, 2010, 3 pages.
Copy of $2^{nd}$ Office Action for Chinese patent application No. 200480011758.X, dated Aug. 7, 2009, 8 pages.
Mexican Official Action for Mexican Patent Application No. PA/a/2005/009253, received on Dec. 7, 2009, 2 pages.
Czechowski, "ATP Technology, A Tool for Monitoring Microbes in Cooling Systems," *American Power Conference*, Chicago, IL, Apr. 10, 1996, 5 pages.
"Cell Analysis in Real-Time," PCI Paint & Coatings Industry, Biocides Equipment, 2003, 19(7):60-62.
"Toxicant Evaluation BIOSCAN® ATP Method," MBO12 0104, MB Procedures, 2001, BetzDearborn—A Division of Hercules Incorporated, 2 pages.
"Analysis of Biofilm Organisms Bioscan® ATP Method," MB013 0104, MB Procedures, 2001, BetzDearborn—A Division of Hercules Incorporated, 4 pages.
"Monitoring of Microbes in Cooling Water BIOSCAN® ATP Method," MB014 0104, MB Procedures, 2001, BetzDearborn—A Division of Hercules Incorporated, 3 pages.
"Standard Test Methods for Nonvolatile and Pigment Content of Electrocoat Baths," Designation: D 5145-90 (Reapproved 1997), American Society for Testing and Materials (ASTM) pp. 581-582.

(Continued)

*Primary Examiner* — Jon P Weber
*Assistant Examiner* — Kailash C Srivastava
(74) *Attorney, Agent, or Firm* — Shumaker & Sieffert, P.A.

(57) ABSTRACT

Use of a micro-organism detection device to rapidly evaluate the presence of microorganisms in an electrocoating process.

8 Claims, No Drawings

(56) References Cited

OTHER PUBLICATIONS

Lee and Deininger, "Rapid quantification of viable bacteria in water using a ATP assay," *American Laboratory News*, 2001, http://www.iscpubs.com/articles/aln/n0110lee.pdf, pp. 24-26.

Wooten, "An inhibition monitor for rapid wastewater screening," Water Environment Federation and Purdue University Industrial wastes Technical Conference, 2000, St. Louis, MO, 10 pages.

* cited by examiner

DETECTING MICRO-ORGANISMS IN AN ELECTROCOATING PROCESS

RELATED APPLICATIONS

This application claims the benefit of priority under 35 USC §119(e)(1) of U.S. Provisional Application No. 60/452,132, filed on Mar. 4, 2003.

TECHNICAL FIELD

This invention relates generally to analyzing electrocoat materials, and more particularly to detecting microorganisms in an electrocoating process.

BACKGROUND

Electrocoat finishing systems have, by nature, many warm and damp areas and thereby provide good conditions for microorganism breeding and growth. A challenge to electrocoat finishers is to minimize and prevent microorganisms from growing within the process. Therefore, electrocoat finishers are mindful of microorganism growth and propagation. To monitor the population or level of microorganisms, manufacturers/finishers intermittently take samples and send them for testing and analysis, only to receive the information days later (e.g. 2-10 days).

As electrocoating operations are typically continuous processes, the time lag between when a representative sample is taken until the time of receiving the analysis creates inefficiency, compromises the quality of manufactured parts, and potentially permits continued growth of microorganisms. Furthermore, after preventive maintenance or scheduled cleanings, practitioners are forced to guess whether the cleaning procedure was effective or not.

Bioluminescence assays have been used in various industries including water treatment facilities, medical laboratories, and food and beverage manufacturing. These assays however, generally analyze materials with very low to negligible amounts of foreign substances that can compromise the accuracy of the analysis. Electrocoating materials, however, pose a challenge due to typically high levels of solids and particulates originating from pigments, resins and other additives.

What is desired is a reliable, relatively low cost method for obtaining quick evaluation of microorganism presence and/or growth in an electrocoat process.

SUMMARY

Certain methods of the invention can advantageously provide rapid analysis of the level of micro-organisms in a sample of electrocoat material obtained from an electrocoating operation. A method of the invention can advantageously eliminate the waiting period between the end of a treatment and receipt of a microbial analysis. Quantitative and qualitative data retrieved by certain methods of the invention can eliminate the guesswork out of electrocoat equipment treatments, such as cleaning procedures. Practicing a method according to embodiments of the invention can provide nearly instantaneous, real-time evaluation of the effectiveness of a treatment so that electrocoat finishers can operate with assured quality and cleanliness. This can result in reductions in the need for frequent treatments and thereby reduce operating costs while increasing the amount of operating up-time.

In an aspect of the invention, a method comprises providing a micro-organism detection device; introducing a liquid sample that includes electrocoat material to the detection device; and rapidly determining the presence of micro-organisms. The liquid sample can be prepared by drawing liquid from a liquid stream within an electrocoating process, or by mixing, suspending, or solubilizing electrocoat material taken from a surface of equipment within the electrocoat process.

In one embodiment, the presence of micro-organisms in the liquid sample can be determined in less than one hour.

In another embodiment, the micro-organism detection device comprises a luminometer.

DEFINITIONS

The following terms are intended to have the following meanings:

"micro-organisms" and "microbial" are used synonomously, to refer to a class of living cells that include, but are not limited to, bacteria, fungi, yeasts, and algae;

"electrocoat material" is any source of liquid, solid, or combinations thereof within an electrocoating process, obtained from a liquid stream or surface of electrocoat equipment or component of an electrocoat process that handles, stores, transports, or processes material;

"liquid sample" is a representative amount of electrocoat material prepared in an analyzable and primarily liquid form; and "process area" is an area within the electrocoating operation that includes the equipment that primarily performs the described function, as well as equipment related to, connected or associated with the primary equipment. For example, a post rinse process area includes the rinse booth as well as the rinse water supply tank, the pipes associated with the booth, sprayers, risers, and any other equipment that feeds, removes, processes or handles post rinse material.

The details of one or more embodiments of the invention are set forth in the accompanying drawings and the description below. Other features, objects, and advantages of the invention will be apparent from the description and drawings, and from the claims.

DETAILED DESCRIPTION OF EMBODIMENTS

It has been found that a micro-organism detection device can be used to obtain very rapid determinations of the presence of microorganisms in materials within an electrocoating process. Advantageously, methods of the invention can be used on samples representative of electrocoat material from liquid streams as well as surfaces within the electrocoating process. Certain devices can also provide nearly instantaneous results as to the level of microbial contamination of a sample.

A variety of devices that work using light monitoring/measuring techniques are useful in the practice of the invention. For example, devices that measure light transmissivity, reflectance, absorbance, etc. can be implemented. Biosensors, such as those devices that incorporate biofluoresence, bioluminescence and other bioassays are also suitable. One system that can be used to detect micro-organisms in electrocoat materials is based on methods that use optical waveguides and immunoassay methods for detecting concentrations of microorganisms in a liquid sample. In another system, direct fluorescent labelling of individual, metabolically active cells using reagent formulation technology can be used, and optionally combined with laser scanning to provide quantitative data as well as a map of where the micro-organisms exist on a collection membrane. Still other techniques that can be used in the practice of the invention are molecular techniques such as fluorescent in situ hybridization, where quantitative detection of specific microorganisms in complex samples with mixed cultures can be achieved.

In one embodiment of the invention, a detection device that is based on adenosine triphosphate (ATP) technology can be used, where an enzymatic reaction produces detectable light. See "ATP Technology, a Tool for Monitoring Microbes in Cooling Systems" by Melvin H. Czechowski (technical paper written for American Power Conference; Chicago, Ill. Apr. 10, 1996) for information on ATP Technology. As known in the art, ATP is a compound that can carry, transfer and store biological energy in microbial cells. It is produced only by living cells and decreases as cells die. The intensity or amount of illumination given off by detected ATP (by reaction in the luciferase reaction) is proportional to the concentration of ATP. This light intensity can then be quantified using a luminometer to provide an indication of the level of microbial cell activity in a sample.

An exemplary method of the invention includes taking a sample from an electrocoating operation and introducing the sample to a micro-organism detection device configured to receive the sample and provide rapid evaluation of the micro-organism content in the sample. In less than an hour, often in less than about five minutes, the device provides an indication as to the presence of micro-organisms in the sample. The indicator can be any type of output signal that can alert a user to detected levels of micro-organisms, such as, for example, a light, a sound, a numerical display, etc. Certain devices can be capable of providing a numerical value that correlates to the level of the micro-organisms present in the sample. Still in other methods, micro-organism detection device can provide a numerical output that requires mathematical conversion of the output value to obtain a corresponding amount or level of micro-organisms present in the sample, provided in standard industry measurements, such as colony forming units per unit of volume (e.g., $CFU/cm^3$).

Liquid samples for analysis in a micro-organism detection device can be obtained from a variety of sources within an electrocoat process, such as liquid streams or surfaces of equipment in the process. Liquid streams within an electrocoating process can include, for example, liquid contained in or flowing in a process area, or equipment associated with the process areas such as a tank, a pipe, a sprayer, etc. Exemplary process areas and associated equipment within an electrocoating operation that may be analyzed for microorganism content include a paint tank, electrocoat bath, permeate, post rinse, deionized water/reverse osmosis (DI/RO) water supply, filter housings, pumps, pump boxes, filter membranes, and many other areas in the operation.

A liquid sample can be obtained directly from a liquid stream by using a sample collection tool provided by the device manufacturer, where the collection tool is typically designed to fit in the detection device with no further manipulation. Alternatively, the liquid sample can be prepared by pulling an amount from the liquid stream (e.g. by drawing or absorbing electrocoat material onto a swab, or into a syringe) and then transferring a sample of the material into a holder fit for introduction to the detection device. Other detection devices and systems can be capable of accepting a sample taken directly from the pulled amount of electrocoat material (e.g., no holder in the device).

Liquid samples for microbial detection analysis can be provided in diluted or undiluted form. Liquid streams of an electrocoat operation can vary in the amount of solids (weight percentage) present in the liquid. For example, liquid streams within an electrocoating process can have as much as 75% solids, such as in certain paints and as low as 0% solids, such as in the DI/RO water. Electrocoat paints can be provided as a raw material (to the electrocoating process) containing varying levels of solids. The concentration of solids can also change as the paint is processed through the electrocoating operation. For example, a paint can be supplied as a raw material having about 70 wt % solids, which then is diluted in a replenishment system down to about 25 wt % solids, possibly even down to about 7 wt %. Because of the various levels of solids (weight percentage) in the numerous liquid streams within an electrocoating operation, it may be necessary to dilute the sample to a sufficiently low level of solids so that an accurate and reliable reading can be obtained by the detection device.

In devices that rely on light measuring techniques such as absorbance, reflectance, transmissivity, etc., solid matter that may interfere with accurate measurement would need to be factored into how the liquid sample is prepared. For example, certain electrocoat material can contain light impacting matter that can absorb, scatter, refract, or reflect light. The amount of such light impacting matter in a liquid sample would therefore need to be adjusted and accounted for, according to the specifications of a detection device.

In an exemplary method that implements a device which relies on light transmissivity (e.g., a luminometer), liquid samples are provided in a sufficiently light transmissive form. The level of light transmissivity required, however, can vary, depending on the detection device, and is typically specified by a device manufacturer. To achieve the recommended light transmissivity level for accurate and reliable analyses, the original, unaltered material drawn from the electrocoat process may need to be diluted. The dilution ratio (electrocoat material:liquid carrier) can vary depending on the type of solids contained in the electrocoat material, where the electrocoat material comprises solids measured according to ASTM D5145-90 (Reapproved 1997). Factors such as the presence of particles, the size, weight, density, opacity and color of such particles, and other characteristics of other solids matter in the material can play a role in the light transmissivity of a sample. Thus, where drawn material comprises darker and denser solids matter that tend to allow very little light through, the material can be diluted to provide a sample having, for example, less than about 10 wt % solids. In an aspect, the material can be diluted so the sample includes less than about 4 wt % solids matter, and in particular, less than about 2 wt % solids matter. Light colored solids matter that have greater light transmissivity can be in liquid samples at higher solids concentrations, such as greater than 50 wt %. Certain paints, when tested under the industry standard test method of ASTM D 5145-90, can include up to 100 wt % solids, yet the solids matter is of such high light transmissivity that dilution may not be necessary to obtain accurate microbial analysis via luminosity.

Components and additives such as pigments and extenders that are included in electrocoat materials also have solids with densities that fall within a wide range. For example, solid matter in an electrocoat material can be from about 1 $g/cm^3$ to about 10 $g/cm^3$. A typical range can be from about 1 to about 4 $g/cm^3$. Depending on the density of solid matter in the sample electrocoat material, the dilution ratio of the electrocoat material to liquid carrier can therefore also be adjusted for light transmissivity. Higher density matter can increase the amount of liquid carrier needed to prepare an analyzable sample; whereas lower density matter can decrease the amount of liquid carrier needed. Accordingly, a balance of all the solid matter attributes (e.g., color, density, weight, size, etc.) can be accounted for when preparing a liquid sample.

Liquid samples for evaluation of microbial contamination can also be prepared to represent electrocoat material obtained from surfaces associated with process areas, such as tank walls, pipe walls, inner surfaces of spray nozzles, valves, etc. It may also be desirable to evaluate microbial content of walls of a facility that houses an electrocoat process. To obtain a representative sample suitable for analysis in a rapid micro-organism detection device, a collection tool can be used to contact the target surface and then the collected matter can be transferred to a container of liquid carrier or solution. The analyzable sample is thereby provided by suspending the collected matter in the solution, or by solubilizing the matter in the liquid carrier. Collecting material for evaluation can be performed using, for example, a cotton swab or a scraping tool. In an exemplary method, a sterile cotton swab can be used to contact an area on the target surface for a sufficient time (e.g., about 10 seconds) to remove superficial matter from the area and have it cling to the swab. In a wet area, the swab can be used to contact the target area and achieve saturation of the material. A swab having collected matter in either form can then be placed in a liquid carrier-filled container (e.g. vial, tube, bottle, jar, flask) and then shaken for a sufficient time (e.g. about 5-10 seconds) to transfer the collected matter from the swab to the liquid carrier. The amount of time necessary to achieve the transfer from the swab to the liquid carrier can vary depending on the amount of collected matter and the attributes (e.g., density, weight, etc.) of the matter. Typically, the transfer can take about 5 to about 10 seconds of vigorous shaking to achieve sufficient transfer, mixing, suspension and/or solubilizing. An amount of the mixed, suspended or solubilized matter is then transferred to a second container configured to be compatible with a micro-organism detection device. The collection procedure can alternatively be performed using any one of a variety of scraping tools such as a knife, a blade, a chisel, etc. The collected superficial matter scraped from a target surface can then be suspended or solubilized as described above and then analyzed in similar fashion.

Suitable liquid carriers for preparing an analyzable liquid sample include, for example, water, alcohol, (e.g. is isopropanol, butanol) glycol ether solvents, acid and amine solubilizers, and other clear solutions. In certain embodiments, liquid carriers that can solubilize or dissolve solid matter found in electrocoat material can be useful.

Any one of a variety of microbial detection devices designed to evaluate liquid samples rapidly can be utilized in methods of the invention where light technology is implemented. Useful devices include, for example, PROFILE® 1 (New Horizons Diagnostics, Inc.; Columbia, Md.), ENLITEN® ATP Assay System (Promega Corp.; Madison, Wis.), and BIOSCAN™ ATP (GE BetzDearborn; Trevose, Pa.), all of which use bioluminescence technology based on ATP. In an exemplary method where a BIOSCAN™ ATP system is used, evaluation of a liquid sample after introducing the sample into the device can be accomplished in less than one hour, often in less than five minutes. The presence of micro-organism contamination can be obtained in even less time, such as one minute.

In use, a method of the invention can detect various micro-organism populations in electrocoat material, including, but not limited to, bacteria, protozoa, molds, yeasts, and algae. Detectable bacterias include those that can grow in an electrocoat operation such as aerobic bacteria, nitrogen cycle bacteria, iron bacteria, legionella bacteria, and sulfate reducing bacteria. Both planktonic populations and sessile life forms can be detected, as they can be drawn into the liquid sample, whether directly or indirectly (e.g. swipe or swab method).

Optionally, regularly scheduled evaluation of microbial contamination can be integrated into operating procedures for an electrocoating operation. Statistically sound sampling plans can also be designed and implemented as part of maintenance, quality control, quality assurance, and regulatory procedures. For example, 40 to 50 samples can be taken over a one to two hour period and analyzed using a micro-organism detection device. Practicing a method of the invention as part of a maintenance protocol (e.g. cleaning or treatment) can provide useful information as to the efficiency and efficacy of the maintenance protocol. This can be accomplished by obtaining samples immediately after the treatment procedure, at locations throughout the process. Repeated evaluations can be monitored by trend and other statistical analyses. An optional data tracking system can be linked with the detection device to store and manipulate analysis readings.

Methods of the invention can also be useful for finding areas of an electrocoat process that have higher contamination levels relative to other process areas. In an exemplary procedure, output readings from adjacently situated process areas can be compared and evaluated. This can be useful when practitioners wish to find the source of the micro-organism growth, or when specific areas within the process are being treated.

A number of embodiments of the invention have been described. Nevertheless, it will be understood that various modifications may be made without departing from the spirit and scope of the invention. Accordingly, other embodiments are within the scope of the following claims.

What is claimed is:

1. A method, comprising:
providing a continuous electrocoating operation, wherein the electrocoating operation comprises a plurality of process areas comprising an electrocoat material, wherein the process areas comprise a first process area and at least one other process area, and wherein the at least one process areas is adjacently situated to the first process area;
taking a first sample of electrocoat material from the first process area and determining with a luminometer a level of microorganisms in the first process area, wherein the luminometer measures illumination emitted from ATP in a population of microorganisms in the first sample, and wherein the level of microorganisms in the first sample is determined in less than 1 hour;
taking at least one second sample of electrocoat material from the at least one other process area and determining with a luminometer a level of microorganisms in the at least one other process area, wherein the luminometer measures illumination emitted from ATP in a population of microorganisms in the second sample, and wherein the level of microorganisms in the second sample is determined in less than 1 hour;
comparing the level of microorganisms in the first sample to the level of microorganisms in the second sample(s) until a source of microorganism growth in the electrocoating operation is identified; and
treating the source of microorganism growth, 2. The method according to claim 1, wherein the level of microorganisms in the sample is determined in less than 5 minutes.

3. The method according to claim 1, wherein the samples are obtained from at least one of a liquid stream source within the process area and a surface in the process area.

4. The method according to claim 1, wherein the samples comprise solid matter having an average density of about 1 g/cm$^3$ to about 4 g/cm$^3$.

5. The method according to claim 1, wherein the sample comprises less than about 10 wt % solids.

6. The method according to claim 1, wherein the sample comprises less than about 4 wt % solids.

7. The method according to claim 1, wherein the sample comprises less than about 2 wt % solids.

8. The method according to claim 1, wherein the luminometer is integrated with a computer-based monitoring system to communicate at least one output therefrom.

* * * * *